(12) United States Patent
Munsterman et al.

(10) Patent No.: US 9,220,905 B2
(45) Date of Patent: *Dec. 29, 2015

(54) SAMPLING INTRINSIC AV CONDUCTION TIME

(71) Applicant: Medtronic, Inc., Minneapolis, MN (US)

(72) Inventors: Nathan P. Munsterman, Andover, MN (US); Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,039

(22) Filed: May 30, 2014

(65) Prior Publication Data

US 2014/0343618 A1  Nov. 20, 2014

Related U.S. Application Data

(63) Continuation of application No. 13/193,747, filed on Jul. 29, 2011, now Pat. No. 8,744,576.

(51) Int. Cl.
*A61N 1/368* (2006.01)
*A61N 1/365* (2006.01)
*A61B 5/042* (2006.01)
*A61B 5/0452* (2006.01)
*A61N 1/362* (2006.01)
*A61B 5/00* (2006.01)

(52) U.S. Cl.
CPC ............ *A61N 1/3682* (2013.01); *A61B 5/0422* (2013.01); *A61B 5/0452* (2013.01); *A61N 1/36507* (2013.01); *A61B 5/686* (2013.01); *A61B 5/6869* (2013.01); *A61N 1/3627* (2013.01)

(58) Field of Classification Search
CPC ... A61N 1/3627; A61N 1/3684; A61N 1/362; A61N 1/36592; A61N 1/3682; A61N 1/36507; A61N 1/3962; A61N 1/368; A61N 1/3756; A61B 5/0452; A61B 5/0472; A61B 5/686
USPC ..................................................... 607/9, 25
See application file for complete search history.

(56) References Cited

U.S. PATENT DOCUMENTS

| | | | |
|---|---|---|---|
| 5,117,824 A | 6/1992 | Keimel et al. | |
| 5,425,750 A | 6/1995 | Moberg | |
| 5,725,561 A | 3/1998 | Stroebel et al. | |
| 5,861,007 A | 1/1999 | Hess et al. | |
| 6,507,756 B1 | 1/2003 | Heynen et al. | |
| 6,792,307 B1 | 9/2004 | Levine et al. | |
| 7,395,113 B2 | 7/2008 | Heruth et al. | |
| 7,593,773 B2 | 9/2009 | Boute et al. | |
| 7,643,878 B1 | 1/2010 | Muller et al. | |
| 7,869,872 B2 | 1/2011 | Sheldon et al. | |
| 2004/0215262 A1 | 10/2004 | Ferek-Petric | |
| 2005/0027323 A1 | 2/2005 | Mulligan et al. | |
| 2007/0093872 A1 | 4/2007 | Chirife et al. | |
| 2007/0191891 A1* | 8/2007 | Burnes et al. | ............... 607/9 |
| 2007/0191892 A1 | 8/2007 | Mullen et al. | |
| 2013/0030486 A1 | 1/2013 | Betzold | |

* cited by examiner

*Primary Examiner* — Rex R Holmes
(74) *Attorney, Agent, or Firm* — Carol F. Barry

(57) ABSTRACT

Methods and/or devices for sampling a patient's intrinsic AV conduction time during cardiac therapy that may, e.g., change the AV delays to values based on the AV delays themselves, previously-sampled intrinsic AV conduction times, and/or one or more other parameters directly related to AV delays to provide a time period during which to measure the patient's intrinsic AV conduction time.

17 Claims, 7 Drawing Sheets

SAMPLING INTRINSIC AV CONDUCTION TIME

This is a continuation of U.S. patent application Ser. No. 13/193,747 filed on Jul. 29, 2011, now U.S. Pat. No. 8,744,576 B2), which is incorporated herein by reference.

The disclosure herein relates to sampling a patient's intrinsic atrioventricular (AV) conduction time during cardiac therapy (e.g., cardiac resynchronization therapy), and further to devices for performing and implementing such sampling.

Cardiac therapy devices (e.g., an implantable medical device (IMD) for performing cardiac resynchronization therapy (CRT)) may provide cardiac therapy (e.g., pacing therapy) and may employ a programmable fixed AV delay in combination with a rate adaptive AV delay feature which adjusts the AV delay based on one or more monitored physiological parameters (e.g., sensed activity such as atrial events, ventricular events, etc.). For example, a cardiac therapy device may periodically measure a patient's intrinsic AV conduction time, or interval, and adjust the timing of right ventricular (RV) and left ventricular (LV) pacing pulses in response to the measured intrinsic AV conduction time, e.g., to optimize cardiac functionality. A patient's intrinsic AV conduction time is the time between an atrial (e.g., right atrium) event (e.g., atrial pace or intrinsic atrial event (depolarization)) and an intrinsic ventricular (e.g., right ventricle) event (depolarization). As used herein, an "intrinsic" ventricular event or conduction is one that occurs or is conducted (e.g., across the AV node of the heart, from the atria to the ventricles, etc.) naturally.

For example, a CRT algorithm (e.g., performed by an IMD) may measure a patient's intrinsic AV conduction time once every minute by forcing delays used for ventricular pacing, such as the paced AV delay (PAV) and the sensed AV delay (SAV), to a long value (e.g., 300 milliseconds (ms), 350 ms, etc.). The PAV delay is an adjustable time period between a paced atrial event and a paced ventricular event (e.g., where a device may optimally deliver a left, right, or bi-ventricular pace), and the SAV delay is an adjustable time period between a sensed atrial event and a paced ventricular event (e.g., where a device may optimally deliver a left, right, or bi-ventricular pace). As such, one of the PAV delay and SAV delay is used depending on whether atrial pacing is utilized (in other words, whether the atrial event is an atrial sense or an atrial pace). Conventionally, the intrinsic AV conduction time measurement has been performed periodically (e.g., every 60 seconds) so that the CRT algorithm can adapt to changes in the patient's intrinsic AV conduction time.

SUMMARY

Exemplary methods and/or devices described herein sample a patient's intrinsic AV conduction time in various ways. Generally, the PAV and SAV delays are changed to measurement delays, which are based the AV delays themselves or one or more parameters directly related to the AV delays, to provide a time period during which to measure the patient's intrinsic AV conduction time. For example, the PAV and SAV delays may be changed to their respective longest acceptable or maximum values (e.g., the longest acceptable delays for the delivery of left, right, or bi-ventricular pacing) to provide a time period during which to measure the patient's intrinsic AV conduction time. Further, for example, the PAV and SAV delays may be increased (e.g., incrementally increased in subsequent measurement cycles if a ventricular event is not sensed) by an offset delay to provide a time period during which to measure the patient's intrinsic AV conduction time. Still further, for example, the PAV and SAV delays may be changed to the last-sampled intrinsic AV conduction time increased by an offset delay to provide a time period during which to measure the patient's intrinsic AV conduction time.

One exemplary implantable medical device for use in delivering cardiac therapy to a patient disclosed herein includes sensing apparatus, a therapy delivery module, and a control module. The sensing apparatus may be configured to monitor a patient's intrinsic AV conduction time and may include at least one electrode. The therapy delivery module may be configured to deliver cardiac therapy to the patient (e.g., ventricular pacing). The control module may be coupled to the sensing apparatus and to the therapy delivery module and may be configured to provide a paced atrioventricular (AV) delay and a sensed AV delay for use in delivering cardiac therapy, to initiate delivery of cardiac therapy based on at least one of the paced AV delay and the sensed AV delay, to sample the patient's intrinsic AV conduction time during the delivery of cardiac therapy, and to set the paced AV delay and the sensed AV delay based on the sampled patient's intrinsic AV conduction time such that ventricular pacing occurs prior to intrinsic ventricular events.

To sample the patient's intrinsic AV conduction time, the control module may be further configured to change the paced AV delay to a first measurement AV delay (e.g., a value that is less than 300 milliseconds) and the sensed AV delay to a second measurement AV delay (e.g., a value that is less than 250 milliseconds) to provide a time period during which to measure the patient's intrinsic AV conduction time and to measure the patient's intrinsic AV conduction time using the sensing apparatus prior to the expiration of one of the paced AV delay and the sensed AV delay. The first measurement AV delay may be based on at least one of the paced AV delay, a previously-sampled intrinsic AV conduction time, and one or more other parameters directly related to the paced AV delay, and the second measurement AV delay may be based on at least one of the sensed AV delay, a previously-sampled intrinsic AV conduction time, and one or more other parameters directly related to the sensed AV delay.

Another exemplary implantable medical device for use in delivering cardiac therapy to a patient disclosed herein includes sensing apparatus, a therapy delivery module, and a control module. The control module may be coupled to the sensing apparatus and to the therapy delivery module and may be configured to provide a paced atrioventricular (AV) delay and a sensed AV delay for use in delivering cardiac therapy, to initiate delivery of cardiac therapy using at least one of the paced AV delay and the sensed AV delay, and to sample the patient's intrinsic AV conduction time during the delivery of cardiac therapy.

To sample the patient intrinsic AV conduction time, the control module may be further configured to change the paced AV delay to a first measurement delay and the sensed AV delay to a second measurement delay to provide a time period during which to measure the patient's intrinsic AV conduction time, and to measure, using the sensing apparatus, the patient's intrinsic AV conduction time prior to the expiration of one of the paced AV delay and the sensed AV delay. The first measurement AV delay may be based on at least one previously-sampled intrinsic AV conduction time (e.g., the last-sampled intrinsic AV conduction time, the mean, mode, or median of a plurality of sampled intrinsic AV conduction times, etc.) increased by a first offset delay, and the second measurement AV delay may be based on at least one previously-sampled intrinsic AV conduction time (e.g., the last-sampled intrinsic AV conduction time, the mean, mode, or median of a plurality of sampled intrinsic AV conduction times, etc.) increased by a second offset delay.

One exemplary method for use in an implantable medical device operable for delivery of cardiac therapy to a patient disclosed herein includes providing a paced atrioventricular (AV) delay and a sensed AV delay for use in delivering cardiac therapy, delivering cardiac therapy using at least one of the paced AV delay and the sensed AV delay, sampling the patient's intrinsic AV conduction time during the delivery of cardiac therapy, and setting the paced AV delay and the sensed AV delay based on the sampled patient's intrinsic AV conduction time such that ventricular pacing occurs prior to intrinsic ventricle events.

The sampling may include changing the paced AV delay to a first measurement AV delay and the sensed AV delay to a second measurement AV delay to provide a time period during which to measure the patient's intrinsic AV conduction time and measuring the patient's intrinsic AV conduction time prior to the expiration of one of the paced AV delay and the sensed AV delay. The first measurement AV delay may be based on at least one of the paced AV delay, a previously-sampled intrinsic AV conduction time, and one or more other parameters directly related to the paced AV delay, and the second measurement AV delay may be based on at least one of the sensed AV delay, a previously-sampled intrinsic AV conduction time, and one or more other parameters directly related to the sensed AV delay.

In one or more exemplary methods and/or devices disclosed herein, the paced AV delay may be adjustable to a maximum paced AV delay and sensed AV delay may be adjustable to a maximum sensed AV delay (e.g., the first measurement AV delay may be equal to the maximum paced AV delay and the second measurement AV delay may be equal to the maximum sensed AV delay).

In one or more exemplary methods and/or devices disclosed herein, the first measurement AV delay may be the paced AV delay increased by an offset delay (e.g., a value that may be less than 50 milliseconds, etc.), and the second measurement AV delay may be the sensed AV delay increased by the offset delay. In at least one embodiment, the offset delay may be increased for use in a subsequent sampling if the patient's intrinsic AV conduction time is not sampled prior to the expiration of one of the paced and sensed AV delays. Further, in at least one embodiment, ventricular pacing may occur if the patient's intrinsic AV conduction time is not sampled prior to the expiration of one of the paced and sensed AV delays.

In one or more exemplary methods and/or devices disclosed herein, the first measurement AV delay may be based on at least one previously-sampled intrinsic AV conduction time (e.g., the last-sampled intrinsic AV conduction time, the mean, mode, or median of a plurality of sampled intrinsic AV conduction times, etc.) increased by a first offset delay and the second measurement AV delay may be based on at least one previously-sampled intrinsic AV conduction time (e.g., the last-sampled intrinsic AV conduction time, the mean, mode, or median of a plurality of sampled intrinsic AV conduction times, etc.) increased by a second offset delay.

The above summary is not intended to describe each embodiment or ever implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
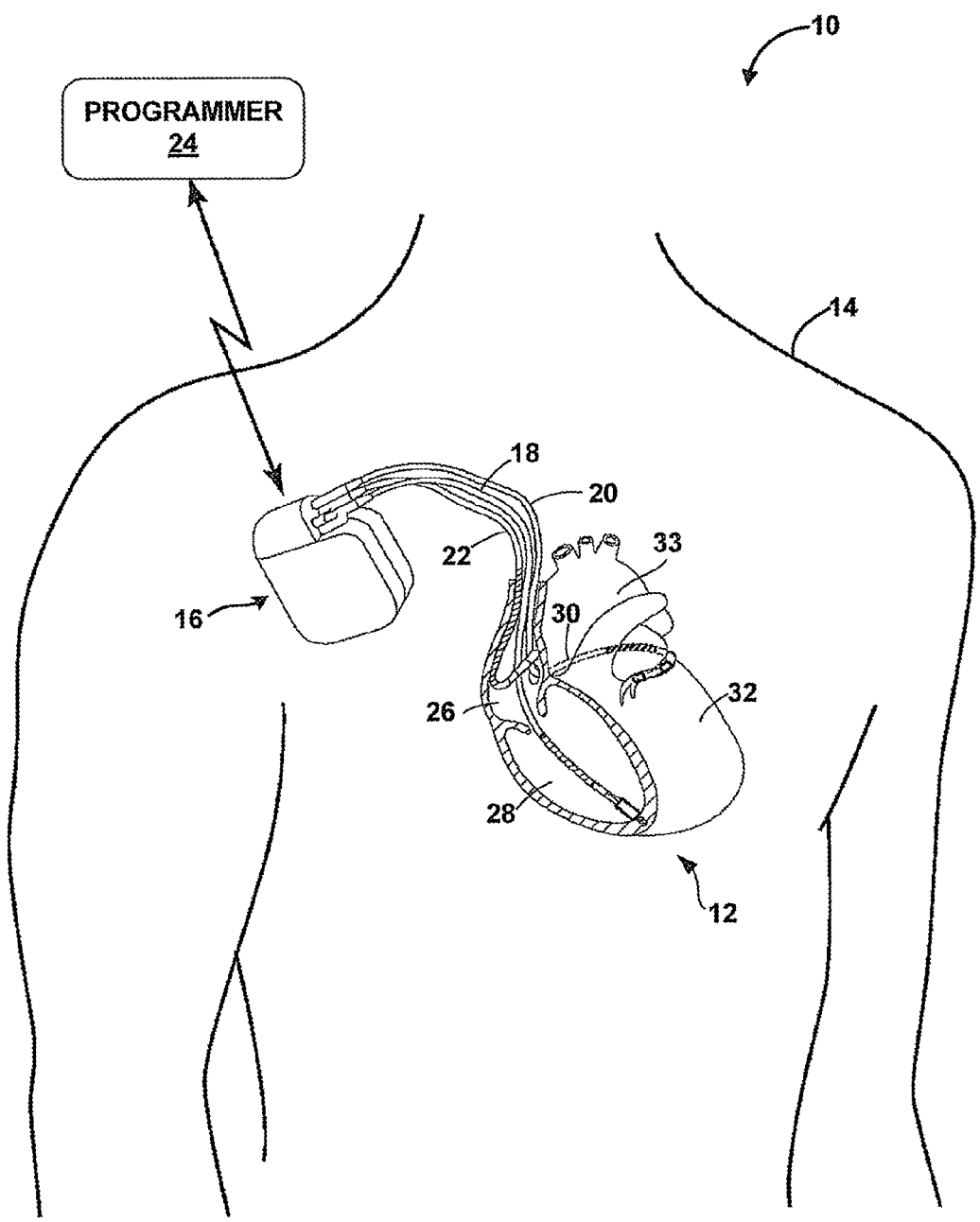
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and devices shall be described with reference to FIGS. 1-7. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used in the delivery of cardiac therapy and/or in the monitoring of one or more physiological parameters of a patient 14. Patient 14 may, but not necessarily, be a human. The exemplary therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals (e.g., stimulation pulses) to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing pulses to the heart 12 based on the electrical signals sensed within the heart 12. The configurations of electrodes used by the IMD 16 for sensing and pacing may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses.

In some examples, the programmer 24 may be a handheld computing device or a computer workstation, which a user, such as a physician, technician, other clinician, and/or patient may use to communicate with the IMD 16. For example, the user may interact with the programmer 24 to retrieve and/or transmit physiological and/or diagnostic information (e.g., one or more physiological parameters, intrinsic AV conduction times, sampling rates, etc.) from the IMD 16.

The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
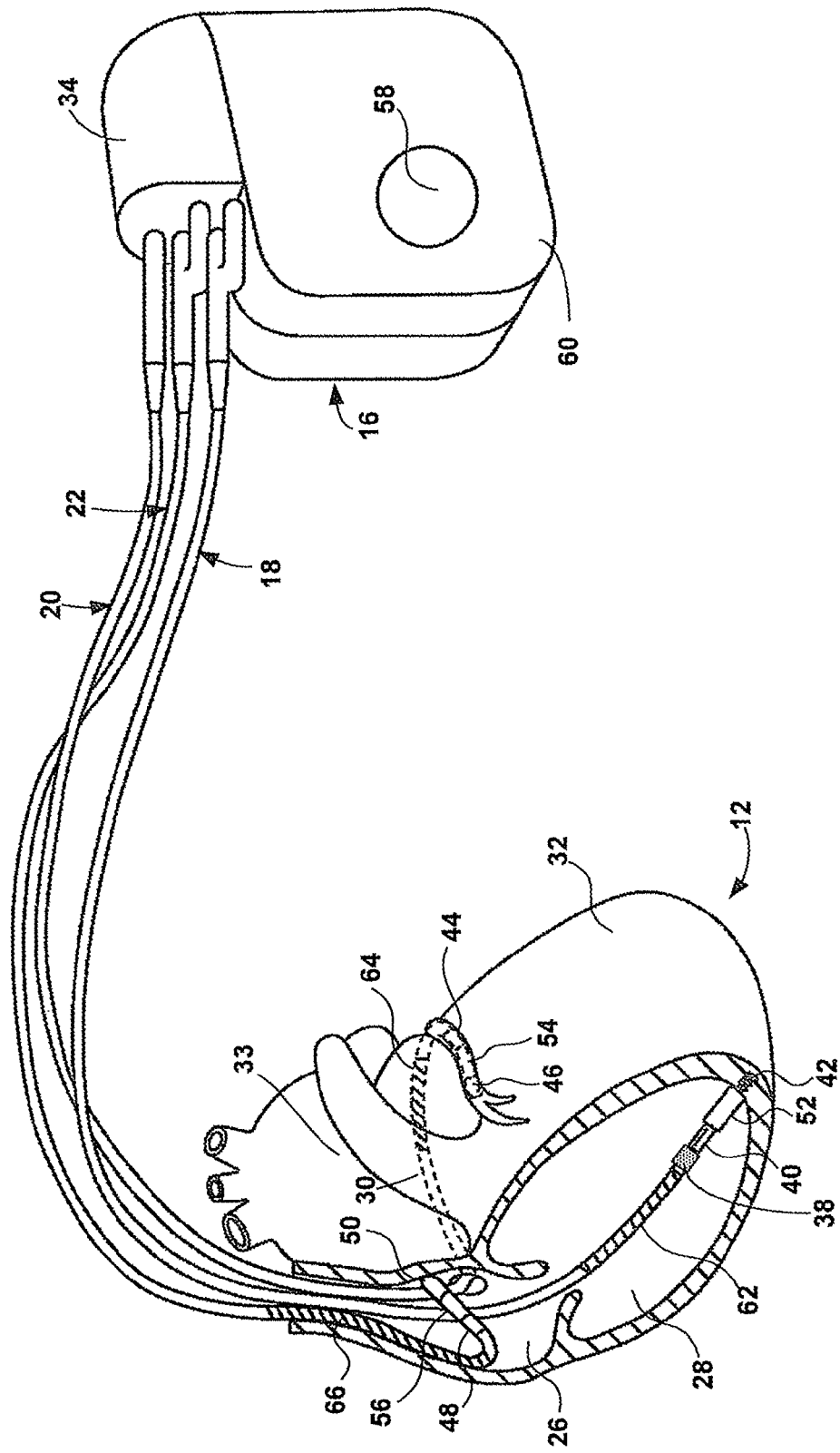
FIG. 2 is a diagram of the IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module, a sensing module, and/or any other modules of the IMD 16 via, a connector block 34. In some examples, the proximal ends of the leads 18, 20, 22 may include electrical contacts that are electrically coupled to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 may include an elongated insulative lead body, which, e.g., may carry a number of concentric coiled conductors, or straight conductors, separated from one another by insulative material. In the illustrated example, a pressure sensor 38 and bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22. As shown in FIG. 2, the pressure sensor 38 is disposed in the right ventricle 28 of the patients heart 12. The pressure sensor 38 may respond to an absolute pressure inside the right ventricle 28, and may be, e.g., a capacitive and/or piezoelectric pressure sensor. In other examples, the pressure sensor 38 may be positioned within other regions of the heart 12 (e.g., the left ventricle) and may monitor pressure within one or more of the other regions of the heart 12, or may be positioned elsewhere within or proximate to the cardiovascular system of the patient 14 to monitor cardiovascular pressure associated with mechanical contraction of the heart.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to a respective one of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12 (e.g., for use in CRT). In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66, and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes.

The pressure sensor 38 may be coupled to one or more conductors within the lead 18. In FIG. 2, the pressure sensor 38 is located more distally on the lead 18 than the elongated electrode 62. In other examples, the pressure sensor 38 may be positioned more proximally than the elongated electrode 62, rather than distal to the electrode 62. Further, the pressure sensor 38 may be coupled to another one of the leads 20, 22 in other examples, or to a lead other than the leads 18, 20, 22 carrying stimulation and sense electrodes. In addition, for example, the pressure sensor 38 may be self-contained device that is implanted within the heart 12, such as within the septum separating the right ventricle 28 from the left ventricle 32, or the septum separating the right atrium 26 from the left atrium 33. In such an example, the pressure sensor 38 may wirelessly communicate with a sensing module of the IMD 16.

The configuration of the therapy system 10 illustrated in FIGS. 1-2 is merely one example. In other examples, a therapy system may include epicardial leads and/or patch electrodes instead of, or in addition to, the transvenous leads 18, 20, 22 illustrated in FIG. 1. Further, in one or more embodiments, the IMD 16 may not be implanted within the patient 14. For example, the IMD 16 may deliver defibrillation shocks and other therapies to the heart 12 via percutaneous leads that extend through the skin of the patient 14 to a variety of positions within, or outside of, the heart 12.

In other examples of therapy systems that provide electrical stimulation therapy to the heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1-2, and an additional lead located within or proximate to the left atrium 33. Still further, other therapy systems may include a single lead that extends from the IMD 16 into the right atrium 26 or the right ventricle 28, or two leads that extend into a respective one of the right ventricle 26 and the right atrium 28.

Figure 3:
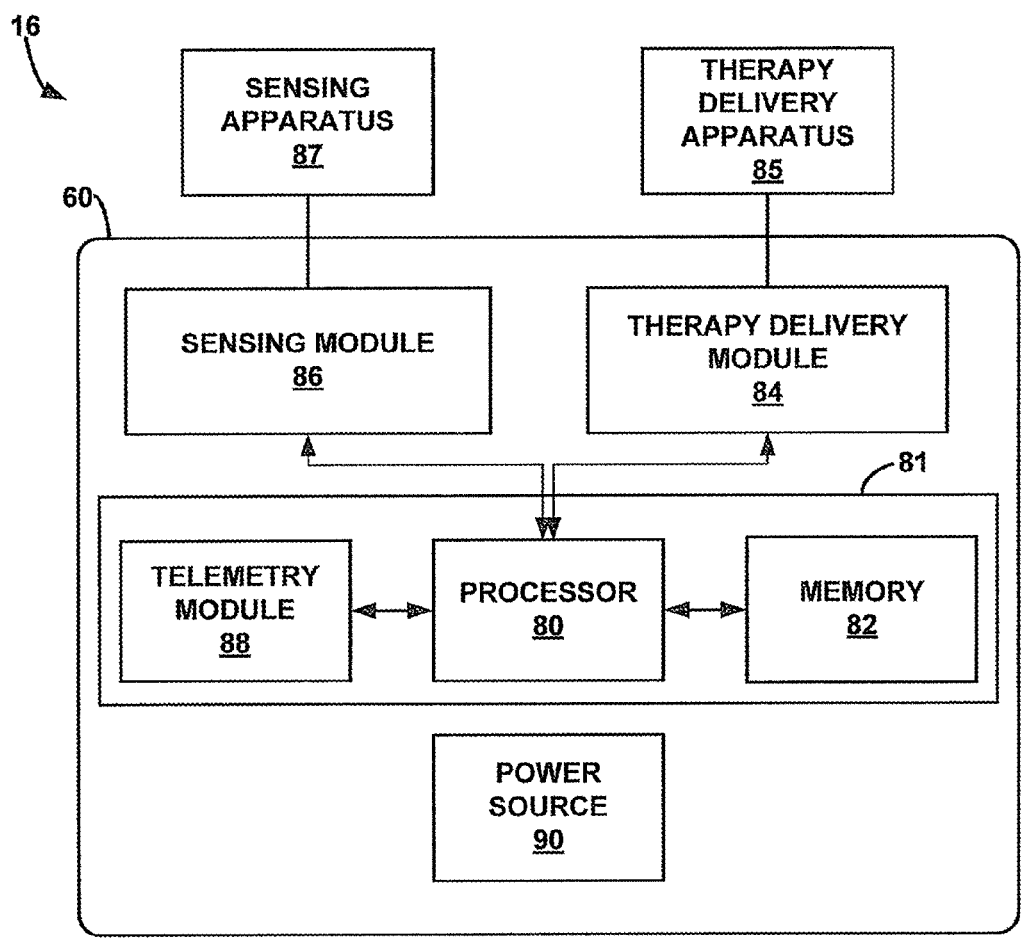
FIG. 3 is a block diagram of the IMD of FIG. 1.

FIG. 3 is a functional block diagram of one exemplary configuration of the IMD 16. As shown, the IMD 16 may include a control module 81, a therapy delivery module 84 (e.g., a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and the control module 81 to perform various functions attributed to the IMD 16 and the control module 81 described herein. Further, the memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the control module 81 herein may be embodied as software, firmware, hardware, or any combination thereof.

The control module 81 controls the therapy delivery module 84 to deliver therapy (e.g., electrical stimulation or pacing therapy) to the heart 12 according to one or more therapy programs, which may be stored in the memory 82. For example, the control module 81 may control the therapy delivery module 84 to deliver electrical pulses with timings, delays, intervals, amplitudes, pulse widths, frequency, and/or electrode polarities specified by the one or more therapy programs.

Further, at least one therapy program stored in the memory 82 may control the sampling of the patient's intrinsic AV conduction time. For example, the cardiac therapy may utilize PAV and SAV delays to, e.g., control the delivery ventricular pacing. To sample a patient's intrinsic AV conduction time, the PAV and SAV delays may be increased to provide a time period during which to measure the patient's intrinsic AV conduction time (e.g., to allow an intrinsic AV conduction to occur prior to pacing one or both ventricles 28, 32). As described herein in more detail with respect to one or more exemplary embodiments and FIGS. 5-7, the PAV and SAV intervals may be changed (e.g., modified or adjusted) in multiple ways to provide a time period during which to measure the patient's intrinsic AV conduction time.

Although not shown, the IMD 16 may further include a notification module that is configured to provide an alert (e.g., to the patient, a clinician, and/or hospital), such as an audio, somatosensory, visual alert, and/or telemetry to an external data collection server. In some cases, the IMD 16 may send the alert to another device, such as the programmer 24, either automatically or upon request. In at least one embodiment, the control module 81 may be configured to initiate an alert using the notification module based on the condition of the IMD 16, indications of lead dislodgement, an assessment of one or more conditions of the patient, etc.

The therapy delivery module 84 is coupled (e.g., electrically coupled) to therapy delivery apparatus 85. The therapy deliver apparatus 85 may include, among other therapy delivery devices, the electrodes 40, 42, 44, 46, 48, 50, 58, 62, 64, 66 of the exemplary systems of FIGS. 1-2 (e.g., via conductors of the respective leads 18, 20, 22) and/or the housing electrode 58. In one or more embodiments, the therapy delivery module 84 may be configured to generate and deliver electrical stimulation therapy to the heart 12. For example, the therapy delivery module 84 may deliver pacing pulses via the ring electrodes 40, 44, 48 coupled to the leads 18, 20, 22, respectively, and/or the helical electrodes 42, 46, 50 of the leads 18, 20, 22, respectively. Further, for example, the therapy delivery module 84 may deliver defibrillation shocks to the heart 12 via at least two of the plurality of electrodes, e.g., electrodes 58, 62, 64, 66. In some examples, the therapy delivery module 84 delivers pacing, cardioversion, and/or defibrillation stimulation in the form of electrical pulses.

The sensing module 86 is coupled (e.g., electrically coupled) to sensing apparatus 87, e.g., to monitor signals from the sensing apparatus 87. The sensing apparatus 87 may include the electrodes 40, 42, 44, 46, 48, 50, 58, 62, 64, 66 to monitor electrical activity of the heart 12, e.g., electrocardiogram (ECG) signals, impedance signals between two or more electrodes (e.g., right and/or left ventricle impedance, subcutaneous impedance, impedance waveform during ejection, impedance waveform during filling, etc.), etc. The ECG signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as AV conduction times, P-R intervals, A-V intervals, or P-Q intervals). QRS-complex morphology, ST segment (i.e., the segment that connects the QRS complex and the T-wave), T-wave changes, QT intervals, electrical vectors, etc. The impedance signals may be used to monitor stroke volume (SV), ejection time (ET), etc.

In at least one embodiment, one channel of the sensing module 86 may include an R-wave amplifier that receives signals from the electrodes 40, 42, which may be used for pacing and sensing in the right ventricle 28 of the heart 12. Another channel may include another R-wave amplifier that receives signals from the electrodes 44, 46, which are used for pacing and sensing proximate to the left ventricle 32 of the heart 12. In some examples, the R-wave amplifiers may take the form of an automatic gain controlled amplifier that provides an adjustable sensing threshold as a function of the measured R-wave amplitude the heart rhythm.

In addition, in at least one embodiment, one channel of the sensing module 86 may include a P-wave amplifier that receives signals from the electrodes 48, 50, which may be used for pacing and sensing in the right atrium 26 of the heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers may be described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of the sensing module 86 may be selectively coupled to the housing electrode 58, or the elongated electrodes 62, 64, 66, with or instead of one or more of the electrodes 40, 42, 44, 46, 48, 50, e.g., for unipolar sensing of R-waves or P-waves in any of the chambers 26, 28, 30, 32 of the heart 12.

In some examples, the sensing module 86 may include a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in the memory 82 as an electrogram (EGM). In some examples, the storage of such EGMs in the memory 82 may be under the control of a direct memory access circuit. The processor 80 may employ digital signal analysis techniques to characterize the digitized signals stored in the memory 82 to detect and classify the patient's heart rhythm from the electrical signals. The processor 80 may detect and classify the heart rhythm of the patient 14 by employing any of the numerous signal processing methodologies known in the art.

If the IMD 16 is configured to generate and deliver pacing pulses to the heart 12, the control module 81 (e.g., the processor 80) may include pacer timing and control apparatus, which may be embodied as hardware, firmware, software, or any combination thereof. The pacer timing and control apparatus may comprise a dedicated hardware circuit, such as an ASIC, separate from other processor components, such as a microprocessor, or a software module executed by a component of the processor 80, which may be a microprocessor or ASIC. The pacer timing and control apparatus may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. In the pacing modes, the first letter identifies either a single-chamber (S), dual-chamber (D) or neither-chamber (O) mode, the second letter corresponds to the chamber(s) sensed, the third letter identifies the pacemaker's response to a sensed event—either triggered (T), inhibited (I) or dual (D), and the fourth letter, if any, indicates a rate responsive feature.

Values or variables e.g., intervals, rates, etc.) defined by the pacer timing and control apparatus within the control module 81 may include PAV delays, SAV delays, measurement PAV delays, measurement SAV delays, maximum PAV delays, maximum SAV delays, adjustable offset delays, atrial and ventricular pacing escape intervals, refractory periods during which sensed P-waves and R-waves are ineffective to restart timing of the escape intervals, and the pulse widths of the pacing pulses.

For example, as described herein, the PAV delay is an adjustable time period between a paced atrial event and a paced ventricular event (e.g., where a device may optimally deliver a ventricular pace), and the SAV delay is an adjustable time period between a sensed atrial event and a paced ventricular event. The PAV and SAV delays may be adjusted, e.g., by a CRT algorithm to optimize cardiac output. As further described herein in more detail with respect to FIGS. 5-7, the PAV and SAV delays may also be adjusted or modified during a measurement or sampling cycle to provide a time period during which to measure the patient's intrinsic AV conduction time.

Further, for example, the maximum PAV and SAV delays (which may be referred to herein as the Block PAV and the Block SAV, respectively) may be the maximum or longest acceptable values for the delivery of ventricular pacing. In other words, the maximum PAV and SAV delays may be described as the maximum delays allowed by the device. Further, the maximum PAV and SAV delays may be selected or predetermined by a clinician, e.g., after or before implantation of the IMD.

Still further, for example, adjustable offset delays may be delays that are adjustable by the exemplary methods described herein, and may be used in the modification or adjustment of the SAV and PAV delays to provide a time period during which to measure the patient's intrinsic AV conduction time (e.g., such as for use in updating parameters used for pacing).

The pacer timing and control apparatus may further define a blanking period, and provide signals from the sensing module 86 to blank one or more channels, e.g., amplifiers, for a period during and after delivery of electrical stimulation to the heart 12. The durations of these intervals may be determined by the processor 80 in response to stored data in the memory 82. The pacer timing and control apparatus may also determine the amplitude of the cardiac pacing pulses.

During pacing, escape interval counters within the pacer timing and control apparatus may be reset upon sensing of R-waves and P-waves. The therapy delivery module 84 may include pacer output circuits that are coupled, e.g., selectively by a switching module, to any combination of the electrodes 40, 42, 44, 46, 48, 50, 58, 62, 64, or 66 appropriate for delivery of a bipolar or unipolar pacing pulse to one of the chambers of the heart 12. The processor 80 may reset the escape interval counters upon the generation of pacing pulses by the therapy delivery module 84, and thereby control the basic timing of cardiac pacing functions, including anti-tachyarrhythmia pacing.

In some examples, the control module 81 (e.g., the processor 80) may operate as an interrupt driven device, and may be responsive to interrupts from the pacer timing and control apparatus, where the interrupts may correspond to various intervals (e.g., PAV and SAV delays, etc.), rates, cardiac occurrence (e.g., sensed P-waves and R-waves, cardiac pacing pulses, etc.). Any necessary mathematical calculations to be performed, e.g., by the processor 80 and any updating of the values or intervals controlled by the pacer timing and control apparatus may take place following such interrupts. A portion of the memory 82 may be configured as a plurality of recirculating buffers, capable of holding series of measured intervals, which may be analyzed, e.g., by the processor 80 in response to the occurrence of a pace or sense interrupt to determine whether the patient's heart 12 is presently exhibiting atrial or ventricular tachyarrhythmia.

In at least one embodiment, if the control module 81 detects an atrial or ventricular tachyarrhythmia based on signals from the sensing module 86, and an anti-tachyarrhythmia pacing regimen is desired, timing intervals for controlling the generation of anti-tachyarrhythmia pacing therapies by the therapy delivery module 84 may be loaded by processor 80 into the pacer timing and control apparatus to control the operation of the escape interval counters therein and to define refractory periods during which detection of R-waves and P-waves is ineffective to restart the escape interval counters.

In at least one embodiment, the IMD 16 may be configured to perform adaptive CRT. Adaptive CRT may be defined as CRT that is automatically optimized based on one or more monitored physiological parameters of the patient 14. One of the monitored physiological parameters that may be used in adaptive CRT is the patient's intrinsic AV conduction time, which, as previously described herein, is the time interval between an atrial event (e.g., in the right atrium) and an intrinsic ventricular event (e.g., in the right ventricle).

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal, and/or external to the IMD 16. The processor 80 may provide the data to be uplinked to the programmer 24 and the control signals for the telemetry circuit within the telemetry module 88, e.g. via an address/data bus. In some examples, the telemetry module 88 may provide received data to the processor 80 via a multiplexer.

In some examples, the processor 80 may transmit atrial and ventricular heart signals (e.g., electrocardiogram signals)

produced by atrial and ventricular sensing circuits within the sensing module 86 to the programmer 24. The programmer 24 may interrogate IMD 16 to receive the heart signals. The processor 80 may store heart signals within the memory 82, and retrieve stored heart signals from the memory 82.

The various components of the IMD 16 may be further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 4:
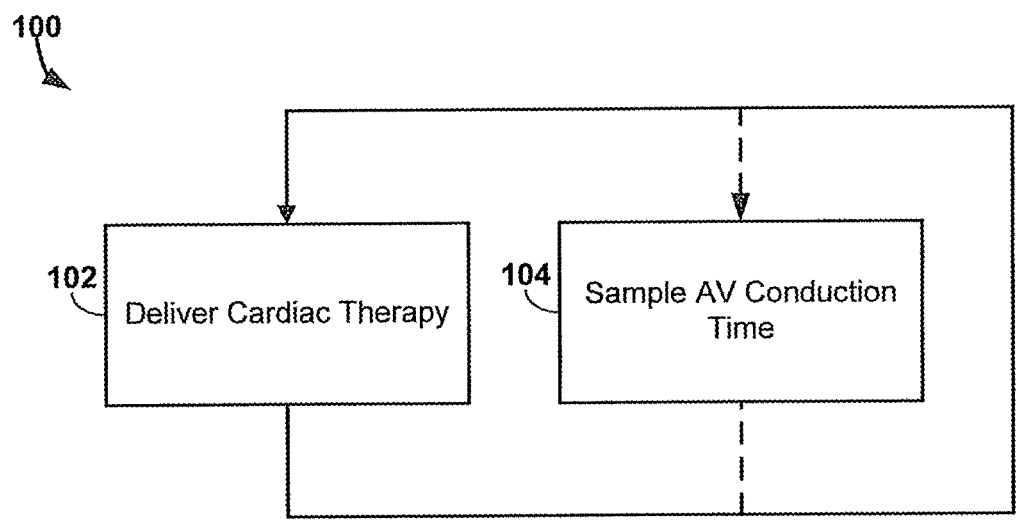
FIG. 4 is a flow chart of a general exemplary method for use in delivering cardiac therapy to a patient and sampling a patient's intrinsic AV conduction time, e.g., using the IMD of FIG. 1.

A generalized method 100 for use in a medical device (e.g., the implantable medical device of FIGS. 1-3) operable for delivery of cardiac therapy (e.g., CRT) to a patent is diagrammatically depicted in FIG. 4. Method 100, as well as the other methods described herein, is intended to illustrate the general functional operation of the devices and/or systems described herein, and should not be construed as reflective of a specific form of software or hardware necessary to practice all of the methods described herein, it is believed that the particular form of software or hardware will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

The method 100 of FIG. 4 includes delivering cardiac therapy 102 to a patient and sampling the patient's intrinsic AV conduction time 104. The delivered cardiac therapy 102 may include, e.g., adaptive cardiac resynchronization therapy (aCRT). aCRT may use, among other things, the patient's intrinsic AV conduction time to optimize the therapy delivered (e.g., pacing therapy) to the patient's heart. In at least one embodiment, delivering cardiac therapy may include determining an optimal AV delay for use in pacing the patient's heart based on the sampled intrinsic AV conduction time, setting the AV delay based on the determined optimal AV delay, and pacing the patient's heart based on the set AV delay. More specifically, if the patient's intrinsic AV conduction time is less than about 170 ms, then ventricular pacing may be delivered about 40 ms before an intrinsic ventricular event should occur (e.g., 40 ms less than the patient's intrinsic AV conduction time), and if the patient's intrinsic AV conduction time is greater than about 170 ms, then ventricular pacing may be delivered more than 40 ms before an intrinsic ventricular event should occur.

To determine the patient's intrinsic AV conduction time (e.g., for use in setting or updating parameters such as the SAV and PAV delays for use in the delivery of cardiac therapy), the method 100 may sample the patient's intrinsic AV conduction time 104. The sampling 104 may be periodic (e.g., cyclical) or recurring sampling, which cycles or recurs at an adjustable sampling rate.

To sample the patient's intrinsic AV conduction time 104, generally, the medical device may delay (e.g., for a single beat, for multiple beats, etc.) the delivery of cardiac therapy 102 (e.g., ventricular pacing) to provide a time period dining which to measure the patient's intrinsic AV conduction time (e.g., increasing the AV delays). To delay the delivery of cardiac therapy 102, the method 100 may change the PAV and SAV delays (upon which cardiac therapy is based) to measurement AV delays. More specifically, the PAV delay may be changed to a first measurement delay, which may be based on at least one of the PAV delay and one or more parameters directly related to the PAV delay (e.g., patient's intrinsic AV conduction time, longest acceptable or maximum PAV delay, etc.), and the SAV delay may be changed to a second measurement delay, which may be based on at least one of the SAV delay and one or more parameters directly related to the SAV delay (e.g., patient's intrinsic AV conduction time, longest acceptable or maximum SAV delay. etc.). In at least one embodiment, the first measurement delay may be about 300 ms, and the second measurement delay may be about 250 ms.

As used herein, one or more parameters that "directly relate" to the SAV and PAV delays are parameters that are utilized to determine (e.g., calculate) the SAV and PAV delays. For example, the maximum SAV and PAV delays limit the length of the SAV and PAV delays, and thus, the maximum SAV and PAV delays are directly related to the SAV and PAV delays. Rather, for example, sampled intrinsic AV conduction times are used to determine the SAV and PAV delays, and thus, sampled intrinsic AV conduction times are directly related to the SAV and PAV delays.

Further, because of slow atrioventricular conduction that may occur due to atrial pacing (as opposed to an intrinsic atrial event), the PAV delay is generally longer than the SAV delay. As such, the first measurement delay may be longer than (e.g., different than) the second measurement delay.

Since the delivery of cardiac therapy (e.g., ventricular pacing) is delayed to measure the patient's intrinsic AV conduction time, the cardiac therapy being delivered to the patient may be disrupted (e.g., become unsynchronized, etc.) Further, the management of the Total Atrial Refractory Period (TARP=Post Ventricular Atrial Refractory Period (PVARP)+SAV) on the beats before, during, and after the measurement, may be disrupted. If TARP is too long, the measurement may result in loss of 1:1 tracking. If TARP is too short, the measurement may initiate a Pacemaker Mediated Tachycardia (PMT).

The exemplary method 100 may improve cardiac therapy disruption e.g., by reducing cardiac therapy disruption) by shortening or limiting the extent at which cardiac therapy is delayed when sampling the patient's intrinsic AV conduction time. Exemplary methods of sampling the patient's AV conduction time 104 are described herein with respect to FIGS. 5-7.

As described herein, conventional aCRT may use (e.g., set) internal limits on the maximum, or longest, acceptable SAV and PAV delays, which may be referred to herein as the Block SAV and the Block PAV. The Block SAV (i.e., the maximum acceptable SAV delay) may be 200 ms and the Block PAV (i.e., the maximum acceptable PAV delay) may be 250 ms. Any sensed values beyond these limits may be considered non-physiologic and the aCRT algorithm may revert to the same behavior as if the patient had complete AV block.

Figure 5:
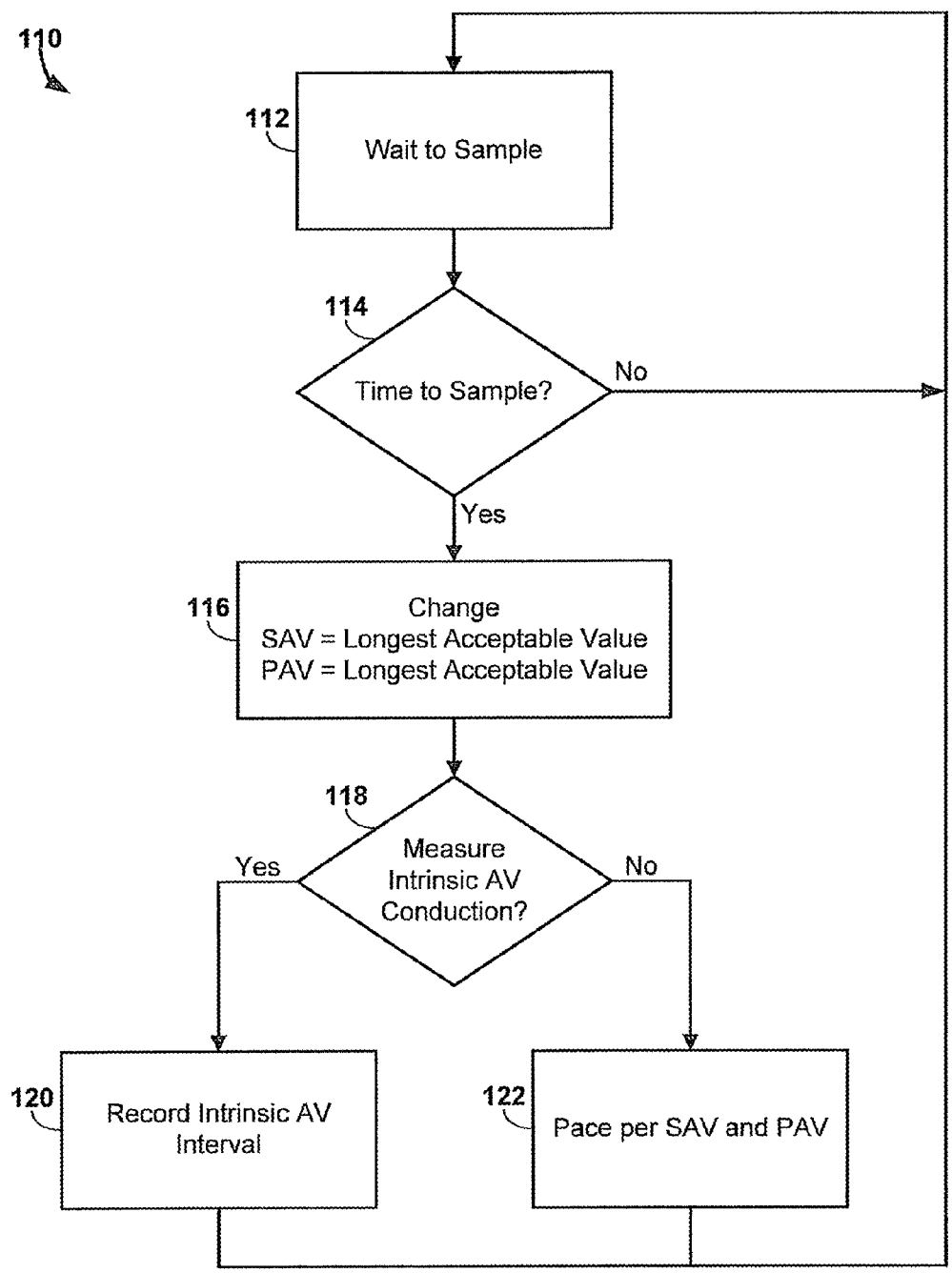
FIG. 5 is a flow chart of an exemplary method for use in sampling a patient's intrinsic AV conduction time.

An exemplary method 110 of sampling a patient's intrinsic AV conduction time depicted in FIG. 5 changes the SAV and PAV delays using the longest acceptable AV delay values to provide a time period during which to measure the patient's intrinsic AV conduction time.

Generally, a patient's intrinsic AV conduction is measured periodically (e.g., every 60 seconds) according to a fixed rate. In at least some embodiments, the rate may be adjustable such as described in "Modification of AV Conduction Time Sampling Rate" U.S. patent application Ser. No. 13/193,735, filed on Jul. 29, 2011 (issued as U.S. Pat. No. 8,583,233 on Nov. 12, 2013), which is incorporated by reference in its entirety.

During the time between measurements, the method 110 waits to sample 112 (e.g., which may be triggered or initiated by an interrupt from the pacer timing and control apparatus within the control module 81) and determines if it is time to sample the patient's intrinsic AV conduction time 114. If it is not time to sample the patient's intrinsic AV conduction time 114, the method 110 continues waiting 112.

If it is time to sample the patient's intrinsic AV conduction time 114, the method 110 proceeds to changing the SAV and PAV delays to their respective longest acceptable or maximum values (e.g., Block SAV=200 ms and Block PAV=250 ms) to provide a time period during which to measure the patient's intrinsic AV conduction time. For example, the SAV may be changed to 200 ms and the PAV may be changed to 250 ms.

During this time period, the method 110 senses ventricular activity, e.g., using electrodes 40, 42 located proximate to a distal end of the lead 18, etc., to measure an intrinsic AV conduction 118. If the time period expires (when one of the PAV or SAV delays expires) without sensing an intrinsic AV conduction, the method 110 may deliver ventricular pacing 122, and proceed to wait to sample 112.

If an intrinsic AV conduction is sensed prior to the expiration of the time period (when one of the SAV and PAV delays expires), the method 110 may record the patient's intrinsic AV conduction 120 (e.g., for use in adjusting one or more parameters such as the SAV and PAV delays for use in delivery of cardiac therapy), and proceed to wait to sample 112.

Exemplary method 110 may be useful because conventional aCRT algorithms may treat all measured values beyond Block SAV and Block PAV values the same (e.g., criteria for AV block), and because it may prevent TARP from getting longer than necessary. For example, when setting the SAV delay to 200 ms and the PAV delay to 250 ms, the worst case TARP is 100 ms shorter than with at least one conventional aCRT implementation, which sets the PAV and SAV values at 300 ms to provide a time period during which to measure the patient's intrinsic AV conduction time.

Figure 6:
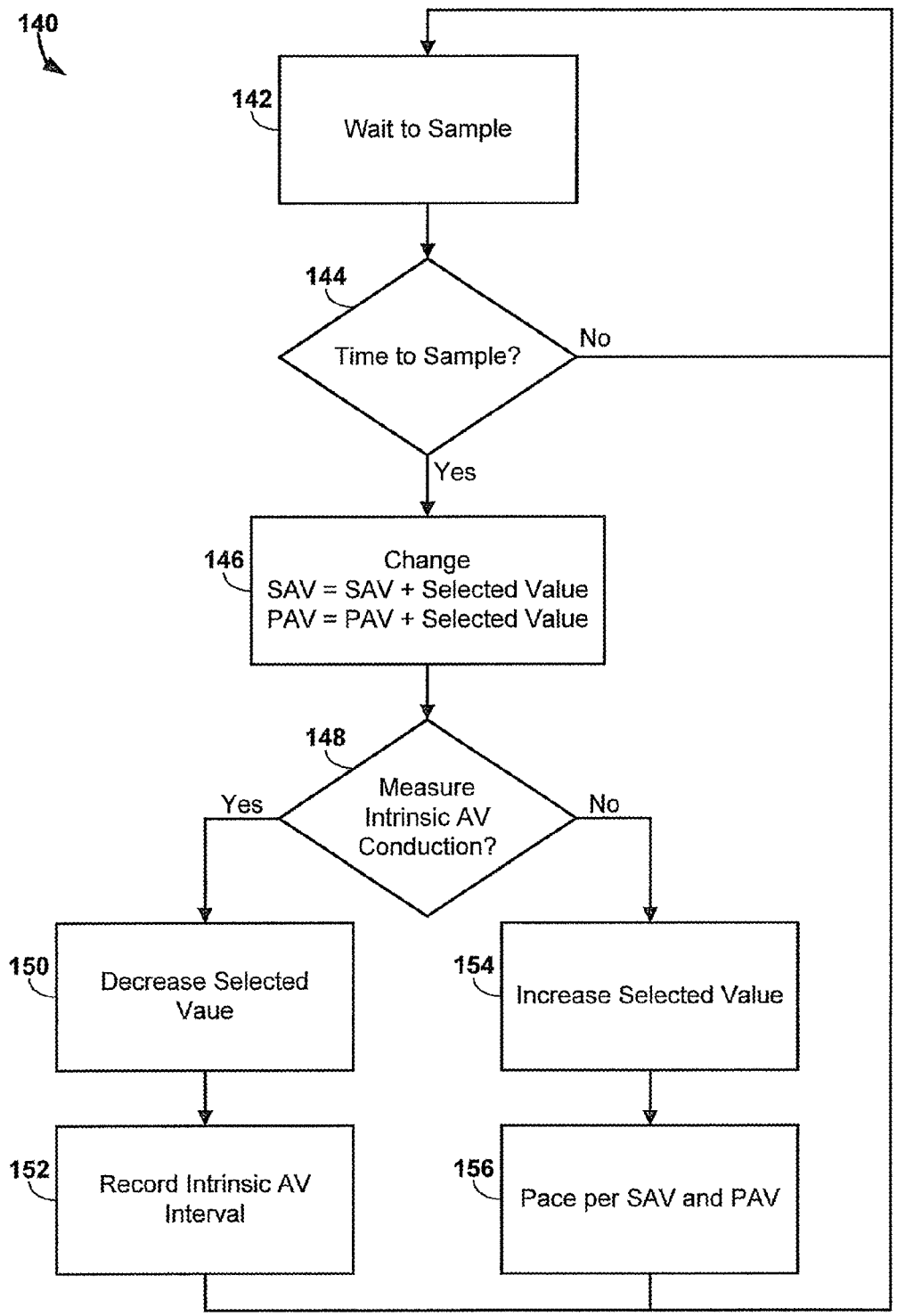
FIG. 6 is a flow chart of another exemplary method for use in sampling a patient's intrinsic AV conduction time.

Another exemplary method 140 of sampling a patient's intrinsic AV conduction time is depicted in FIG. 6. Generally, method 140 Changes the SAV and PAV delays by adding a selected value to each of the SAV and PAV delays to provide a time period during which to measure the patient's intrinsic AV conduction time.

Processes 142, 144 of method 140 may be substantially similar to the processes 112, 114, respectively, described herein with reference to FIG. 5. If it is time to sample the patient's intrinsic AV conduction time 144, the method 140 proceeds to increasing the SAV and PAV delays by a selected value to provide a time period during which to measure the patient's intrinsic AV conduction time. In other words, each of the SAV and PAV delays are changed to a value that is itself (in other words, the current operating value) plus the selected value. For example, if the selected value is 35 ms and the PAV delay is presently 180 ms, the PAV delay may be changed to 215 ms. Further, for example, if the selected value is 55 ms and the PAV delay is presently 180 ms, the PAV delay may be changed to 235 ms. Still further, for example, if the selected value is 10 ms and the PAV delay is presently 180 ms, the PAV delay may be changed to 190 ms.

The "selected value" may also be referred to as an "offset delay." The selected value may be greater than or equal to about 5 ms, about 10 ms, about 12.5 ms, about 15 ms, about 20 ms, about 25 ms, about 30 ms, about 35 ms, about 40 ms, about 45 ms, about 50 ms, etc. Further, the selected value may be less than or equal to about 20 ms, about 25 ms, about 30 ms, about 35 ms, about 40 ms, about 45 ms, about 50 ms, about 60 ms, about 70 ms, about 80 ms, about 90 ms, about 100 ms, etc.

During this time period, the method 140 senses ventricular activity, e.g., using electrodes 40, 42 located proximate to a distal end of the lead 18, etc., to measure an intrinsic AV conduction 148. If the time period expires (e.g., when one of the PAV or SAV delays expires) without sensing an intrinsic AV conduction, the method 140 may increase the selected value or offset delay 154 (e.g., for use in a subsequent sampling of intrinsic AV conduction time), deliver ventricular pacing 156, and proceed to waiting to sample 112. The selected value is increased 154 such that the time period to sense an intrinsic AV conduction will be increased for use in the next sampling attempt. The selected value may be increased 154 by a time value greater than or equal to about 1 ms, about 2 ms, about 3 ms, about 4 ms, about 5 ms, about 7.5 ms, about 10 ms, about 12.5 ms, about 15 ms, about 20 ms, about 30 ms, etc. Further, the selected value may be increased 154 by a time value less than or equal to about 15 ms, about 20 ms, about 30 ms, about 40 ms, about 50 ms, etc. In at least one embodiment, the selected value may be about 10 ms. Although processes 154, 156 are shown in FIG. 6 as being consecutive to one another, they may occur in any order or simultaneously.

If an intrinsic AV conduction is sensed prior to the expiration of the time period (when one of the SAV and PAV delays expires), the method 140 may decrease the selected value or offset delay 150, record the patient's intrinsic AV conduction 152 (e.g. for use in adjusting one or more parameters such as PAV and SAV delays used in the delivery of cardiac therapy), and proceed to wait to sample 142. The selected value is decreased 150 such that the time period to sense an intrinsic AV conduction will be decreased for use in the next sampling attempt. The selected value may be decreased 150 by a value greater than or equal to about 1 ms, about 2 ms, about 3 ms, about 4 ms, about 5 ms, about 7.5 ms, about 10 ms, about 12.5 ms, about 15 ms, etc. Further, the selected value may be decreased 150 by a value less than or equal to about 10 ms, about 12.5 ms, about 15 ms, about 20 ms, about 25 ms, about 30 ms, etc. Although processes 150, 152 are shown in FIG. 6 as being consecutive to one another, they may occur in any order or simultaneously.

In effect, the exemplary method 140 performs sampling by lengthening the operating SAV and PAV intervals slightly beyond the delays at which an aCRT algorithm is trying to operate. For example, an objective of aCRT is to pace the ventricle sooner than the patient's intrinsic AV conduction time using a piece-wise linear characteristic (e.g., that starts with a 40 to 50 ms offset and becomes more aggressive when the patient's AV conduction time is greater than 170 ms) If, for example, the aCRT algorithm is trying to pace the ventricle 50 ms sooner than the patient's intrinsic AV conduction time, the method 140 may lengthen the current operating AV interval by 60 ms over time until a ventricular sense occurs.

More specifically, if a ventricular sense occurs before a ventricular pace, the measurement will occur. On the other hand, if ventricular pace occurs before a ventricle sense, the method 140 will not have measured the intrinsic AV conduction time but has determined the current operating PAV or SAV delay is too short (too aggressive, too much offset) to provide a time period during which to measure the patient's intrinsic AV conduction time (e.g., the patient's AV conduction time is longer than the PAV or SAV delays that were used for measurement). As such, the method 140 may increase the PAV and SAV delays by a longer selected value or offset delay (e.g., 10 ms) for the next measurement. Over time (e.g., over consequent sampling cycles in which the intrinsic AV conduction time is not measured), the SAV and PAV delays will be increased by a value that provides enough time for an intrinsic ventricular sense, and therefore, the patient's intrinsic AV conduction time may be measured.

In at least one embodiment, if the time period expires during the sampling beat (e.g., when one of the PAV or SAV delays expires) without sensing an intrinsic AV conduction, the next sample may be performed early, and prior to the next scheduled sample. For example, as described herein, the intrinsic AV conduction time sampling rate may be one sample per 60 seconds. If an intrinsic AV conduction time was not measured during the sample beat, the method 140 may increase the sampling rate or perform another sample prior to the expiration of the 60 second period (as determined by the intrinsic AV conduction time sampling rate). For instance, the method 140 may conduct another measurement in the next heart beat or a selected number of heart beats. Further, for instance, the method 140 may conduct another measurement after a selected time period, e.g., 5 seconds, 10 seconds, 15 seconds, 20 seconds, 25 seconds, etc.

Figure 7:
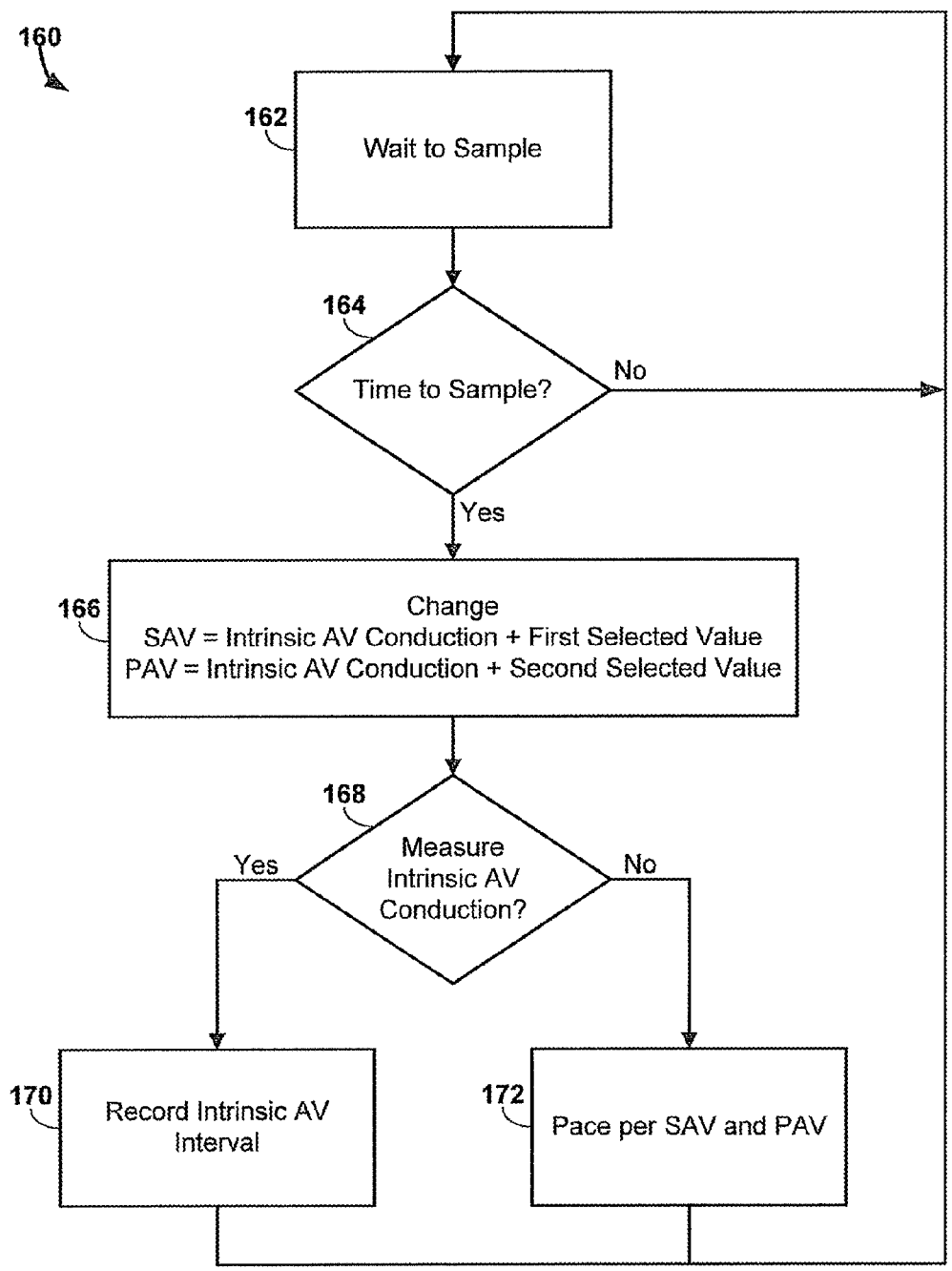
FIG. 7 is a flow chart of still another exemplary method for use in sampling a patient's intrinsic AV conduction time.

Another exemplary method 160 of sampling a patient's intrinsic AV conduction time is depicted in FIG. 7. Generally, method 160 changes the SAV and PAV delays to a previously measured intrinsic AV conduction time (e.g., the last measured intrinsic AV conduction time) plus a selected value or offset value to provide a time period during which to measure the patients intrinsic AV conduction time. In at least one embodiment, method 160 could operate using the results of the last measurement or a statistical combination of more than one previous measurement (e.g., median, mode, mean, etc.). Further, the exemplary method 160 may further fit within conventional aCRT's median buffer concept that operates from multiple, prior measurements rather than just one for adjustment decisions.

Processes 162, 164, 170, 172 of method 140 may be substantially similar to the processes 112, 114, 120, 122, respectively, described herein with reference to FIG. 5, and as such, will not be further described. If it is time to sample the patient's intrinsic AV conduction time 164, the method 160 proceeds to changing the PAV delay to the last measured intrinsic AV conduction time plus a first selected value (or first offset delay) and the SAV delay to the last measured intrinsic AV conduction time plus a second selected value (or second offset delay) to provide a time period during which to measure the patient's intrinsic AV conduction time. For example, if the last measured intrinsic AV conduction time is 100 ms and the first selected value is 15 ms, the SAV delay may be changed to 115 ms.

Further, in one or more embodiments, instead of using the last measured intrinsic AV conduction time, or one or more previously measured intrinsic AV conduction times, to change the AV delays, an average of the patient's intrinsic AV conduction time over a time period (e.g., about 10 minutes, about 20 minutes, about 30 minutes, about 45 minutes, about 1 hours, about 2 hours, about 3 hours, about 6 hours, about 12 hours, about 24 hours) may be utilized. Still further, in one or more embodiments, instead of using the last measured intrinsic AV conduction time to change the AV delays, the patients intrinsic AV conduction time may be logged into a profile such that an average of the patient's intrinsic AV conduction time may be known for a particular time of day, and the average based on the time of day may be utilized.

Each of the "first selected value" and the "second selected value" may also be referred to as "offset delays." Each of the first selected value and the second selected value may be greater than or equal to about 5 ms, about 10 ms, about 12.5 ms, about 15 ms, about 20 ms, about 25 ms, about 30 ms, about 35 ms, about 40 ms, about 45 ms, about 50 ms, etc. Further, each of the first selected value and the second selected value may be less than or equal to about 30 ms, about 35 ms, about 40 ms, about 45 ms, about 50 ms, 60 ms, about 70 ms, about 80 ms, about 90 ms about 100 ms, etc.

In at least one embodiment, method 160 may further include processes that increase or decrease the first and the second selected values based on whether the intrinsic AV conduction time was measured (e.g., if a ventricular sense occurred prior to the expiration of the PAV and SAV delays) similar to the processes 150, 154 described herein with reference to FIG. 6.

The methods and/or techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for use in delivering cardiac therapy to a patient comprising:
sensing apparatus configured to monitor a patient's intrinsic AV conduction time, wherein the sensing apparatus comprises at least one electrode;
a therapy delivery module configured to deliver cardiac therapy to the patient; and
a control module coupled to the sensing apparatus and to the therapy delivery module and configured to:
provide a paced atrioventricular (AV) delay and a sensed AV delay for use in delivering cardiac therapy, initiate delivery of cardiac therapy based on at least one of the paced AV delay and the sensed AV delay, sample the patient's intrinsic AV conduction time during the delivery of cardiac therapy, wherein, to sample the patient's intrinsic AV conduction time, the control module is further configured to:

change the paced AV delay to a first measurement AV delay and the sensed AV delay to a second measurement AV delay to provide a time period during which to measure the patient's intrinsic AV conduction time, wherein the first measurement AV delay is the paced AV delay increased by an adjustable offset delay, and wherein the second measurement AV delay is the sensed AV delay increased by an adjustable offset delay, and measure the patient's intrinsic AV conduction time using the sensing apparatus prior to the expiration of one of the paced AV delay and the sensed AV delay; and set the paced AV delay and the sensed AV delay based on the sampled patient's intrinsic AV conduction time such that ventricular pacing occurs prior to intrinsic ventricular events.

2. The device of claim 1, wherein the paced AV delay is adjustable to a maximum paced AV delay, wherein the sensed AV delay is adjustable to a maximum sensed AV delay, and wherein the first measurement AV delay is equal to the maximum paced AV delay and the second measurement AV delay is equal to the maximum sensed AV delay.

3. The device of claim 1, wherein the first measurement AV delay is less than 300 milliseconds.

4. The device of claim 1, the second measurement AV delay is less than 250 milliseconds.

5. The device of claim 1, wherein, to sample the patient's intrinsic AV conduction time, the control module is further configured to decrease the offset delay for use in a subsequent sampling if the patient's intrinsic AV conduction time is sampled prior to the expiration of one of the paced and sensed AV delays.

6. The device of claim 1, wherein the offset delay is less than 50 milliseconds.

7. The device of claim 1, wherein, to sample the patient's intrinsic AV conduction time, the control module is further configured to increase the offset delay for use in a subsequent sampling if the patient's intrinsic AV conduction time is not sampled prior to the expiration of one of the paced and sensed AV delays.

8. The device of claim 1, wherein the cardiac therapy using at least one of the paced AV delay and the sensed AV delay comprises ventricular pacing if the patient's intrinsic AV conduction time is not sampled prior to the expiration of one of the paced and sensed AV delays.

9. A method for use in an implantable medical device operable for delivery of cardiac therapy, wherein the method comprises:

providing a paced atrioventricular (AV) delay and a sensed AV delay for use in delivering cardiac therapy;

delivering cardiac therapy using at least one of the paced AV delay and the sensed AV delay;

sampling the patient's intrinsic AV conduction time during the deliver of cardiac therapy, wherein the sampling comprises:

changing the paced AV delay to a first measurement AV delay and the sensed delay to a second measurement AV delay to provide a time period during which to measure the patient's intrinsic AV conduction time, wherein the first measurement AV delay is the paced AV delay increased by an adjustable offset delay, and wherein the second measurement AV delay is the sensed AV delay increased by an adjustable offset delay, and measuring the patient's intrinsic AV conduction time prior to the expiration of one of the paced AV delay and the sensed AV delay; and setting the paced AV delay and the sensed AV delay based on the sampled patient's intrinsic AV conduction time such that ventricular pacing occurs prior to intrinsic ventricle events.

10. The method of claim 9, wherein the paced AV delay is adjustable to a maximum paced AV delay, wherein the sensed AV delay is adjustable to a maximum sensed AV delay, and wherein the first measurement AV delay is equal to the maximum paced AV delay and the second measurement AV delay is equal to the maximum sensed AV delay.

11. The method of claim 9, wherein the first measurement AV delay is less than 300 milliseconds.

12. The method of claim 9, wherein the second measurement AV delay is less than 250 milliseconds.

13. The method of claim 9, wherein, to sample the patient's intrinsic AV conduction time, the control module is further configured to decrease the offset delay for use in a subsequent sampling if the patient's intrinsic AV conduction time is sampled prior to the expiration of one of the paced and sensed AV delays.

14. The method of claim 9, wherein the offset delay is less than 50 milliseconds.

15. The method of claim 9, wherein sampling the patient's intrinsic AV conduction time during the delivery of cardiac therapy further comprises increasing the offset delay for use in a subsequent sampling if the patient's intrinsic AV conduction time is not sampled prior to the expiration of one of the paced and sensed AV delays.

16. The method of claim 9, wherein delivering cardiac therapy using at least one of the paced AV delay and the sensed AV delay comprises ventricular pacing if the patient's intrinsic AV conduction time is not sampled prior to the expiration of one of the paced and sensed AV delays.

17. An implantable medical device for use in delivering cardiac therapy to a patient comprising:

sensing apparatus configured to monitor a patient's intrinsic AV conduction time, wherein the sensing apparatus comprises at least one electrode;

a therapy delivery module configured to deliver cardiac therapy to the patient; and a control module coupled to the sensing apparatus and to the therapy delivery module and configured to:

provide a paced atrioventricular (AV) delay and a sensed AV delay for use in delivering cardiac therapy, initiate delivery of cardiac therapy based on at least one of the paced AV delay and the sensed AV delay, and sample the patient's intrinsic AV conduction time during the delivery of cardiac therapy, wherein, to sample the patient's intrinsic AV conduction time, the control module is further configured to:

change the paced AV delay to a first measurement AV delay and the sensed AV delay to a second measurement AV delay to provide a time period during which to measure the patient's intrinsic AV conduction time, wherein the first measurement AV delay is the paced AV delay increased by an adjustable offset delay, wherein the second measurement AV delay is the sensed AV delay increased by the adjustable offset delay, and measure the patient's intrinsic AV conduction time using the sensing apparatus prior to the expiration of one of the paced AV delay and the sensed AV delay.

* * * * *